United States Patent [19]

Raphael et al.

[11] 4,414,416

[45] Nov. 8, 1983

[54] CERTAIN DIACETYL-AMINO-PHENOLIC DERIVATIVES

[75] Inventors: Richard A. Raphael; Stephen C. Eyley; Stephen C. W. Coltman, all of Loughborough, England

[73] Assignee: Fisons Limited, London, England

[21] Appl. No.: 340,974

[22] Filed: Jan. 20, 1982

Related U.S. Application Data

[62] Division of Ser. No. 212,331, Dec. 2, 1980, Pat. No. 4,328,341.

[30] Foreign Application Priority Data

Dec. 7, 1979 [GB] United Kingdom ................ 7942248

[51] Int. Cl.³ ..................... C07C 87/50; C07D 311/24
[52] U.S. Cl. ..................................... 564/443; 549/402

[58] Field of Search ......................... 564/443; 549/402

[56] References Cited

PUBLICATIONS

Fel'dman et al., Zhur. Obsch. Khim., 23, pp. 2043–2046, (1953).

*Primary Examiner*—Alan L. Rotman
*Attorney, Agent, or Firm*—Merriam, Marshall & Bicknell

[57] ABSTRACT

There is described a process for the production of a 1,4-dihydro-4-oxo-quinoline-2-carboxylic acid, or a salt, ester or amide thereof, which comprises cyclization of a corresponding 2-aminobenzoyl pyruvic acid or an ester thereof, and if desired or necessary converting the resulting product to an appropriate salt, ester or amide thereof, or vice versa.

3 Claims, No Drawings

CERTAIN DIACETYL-AMINO-PHENOLIC DERIVATIVES

This is a division of application Ser. No. 212,331, filed Dec. 2, 1980 now U.S. Pat. No. 4,328,341.

This invention relates to a novel process and novel compounds.

The most generally used method for the production of 1,4-dihydro-4-oxo-quinoline-2-carboxylic acids employs reaction of an aniline with dimethyl acetylene dicarboxylate, an expensive and hazardous reagent, followed by high temperature cyclisation in diphenyl ether ($\sim$250°) (unpleasant) or lower temperature cyclisation in polyphosphoric acid, which latter is very awkward to use on a large scale. Yields can be very variable and unreliable at both stages of this process and the cyclisations can form a fused chain with either of the ortho positions on the benzene ring thus leading to intractable mixtures isomeric products.

We have now found a process for the production of 1,4-dihydro-4-oxo-quinoline-2-carboxylic acids which uses cheap and readily available reagents, and which is easily handled in plant. This new process can, in particular, be used for the synthesis of pharmaceutically useful dicarboxypyranoquinolones, providing a method in which both the heterocyclic rings are formed at the same time, and in an unambiguous manner, thus affording considerable advantages in time, effort and cost over previous multistep methods for the synthesis of such compounds. More particularly by reducing the number of steps, and avoiding costly procedures such as high pressure liquid chromatography, in the synthesis of the pyranoquinolinones the overall yield can be enhanced (in some cases more than tripled), and the capital cost of the plant required can be decreased.

According to the invention we provide a process for the production of a 1,4-dihydro-4-oxo-quinoline-2-carboxylic acid, or a salt, ester or amide thereof, which comprises cyclisation of a corresponding 2-aminobenzoyl pyruvic acid or an ester thereof, and if desired or necessary converting the resulting product to an appropriate salt, ester or amide thereof, or vice versa.

The cyclisation may be carried out by heating, or under basic or neutral conditions. It is however preferred to carry out the cyclisation in the presence of an acid, e.g. hydrochloric acid, and in a solvent which is inert under the reaction conditions, e.g. a lower alkanol such as ethanol. Hydrochloric acid may be used either in gaseous or aqueous form, e.g. dilute or concentrated aqueous form. We particularly prefer to use at least one mole of HCl per mole of aminobenzoyl pyruvic acid. The reaction may be carried out from about 0° to 150° C., preferably 30° to 80° C., e.g. the reflux temperature of the reaction mixture. The reaction can conveniently be carried out for 1 to 180, and preferably 5 to 90, minutes. The ester group is preferably a C 1 to 6 alkoxy ester group, e.g. an ethyl ester group.

The 2-aminobenzoyl pyruvic acid starting material may be made by reacting a corresponding 1-(2'-aminophenyl)ethanone with a compound of formula I,

R'CZ—COOH    I or an ester thereof, in which

R' is a suitable leaving group, e.g. an alkoxy, halo, amino, alkylamino, substituted amino (e.g. an arylsulphonylamino group) or substituted alkylamino group, reactive with the carbanion of the -COCH₃ group of the 1-(2'-aminophenyl)ethanone, and Z is a carbonyl oxygen atom, or may represent two halogen atoms, and if necessary hydrolysing the resulting compound to produce the desired starting material.

Preferred compounds of formula I are di- C 1 to 6 alkyl oxalates, e.g. diethyl oxalate.

The process of the invention is particularly adapted to the production of pyranoquinolones, e.g. compounds of formula II,

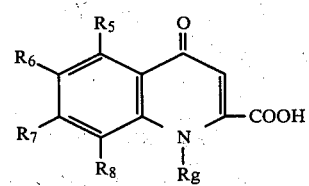

and pharmaceutically acceptable salts, esters and amides thereof, in which an adjacent pair of $R_5$, $R_6$, $R_7$ and $R_8$ form a chain —COCH=C(COOH)—O—, and the remainder of $R_5$, $R_6$, $R_7$ and $R_8$, which may be the same or different, each represent hydrogen, hydroxy, alkyl, halogen, alkenyl, alkoxy, or —NR₁R₂ in which R₁ and R₂, which are the same or different, are each hydrogen or alkyl, and Rg is hydrogen, alkyl, alkenyl or phenyl-alkyl.

Thus according to a preferred feature of the invention we provide a process for the production of a compound of formula II, or a pharmaceutically acceptable salt, ester or amide thereof, which comprises cyclisation of a compound of formula III,

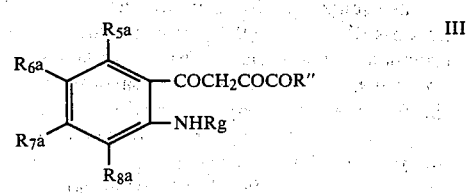

in which $R_{5a}$, $R_{6a}$, $R_{7a}$ and $R_{8a}$ have the same significances as $R_5$, $R_6$, $R_7$ and $R_8$ above, save that an adjacent pair of $R_{5a}$, $R_{6a}$, $R_{7a}$ and $R_{8a}$, may together either represent the chain —COCH=C(COOH)—O— or an ester thereof, or the pairs of groups —COCH₂COCR''; and —OM or a halogen atom, R'' represents —OM or a group which is hydrolysable thereto, M represents hydrogen or an alkali metal, and Rg is as defined above, and if desired or necessary converting the resulting compound to a pharmaceutically acceptable salt, ester or amide thereof, or vice versa.

We particularly prefer to form the nitrogen and the oxygen heterocyclic rings simultaneously. Thus a preferred embodiment of the invention comprises cyclisation of a compound of formula III in which an adjacent pair of $R_{5a}$, $R_{6a}$, $R_{7a}$ and $R_{8a}$ represent the pair of groups —COCH₂COCR'', and —OM.

A further preferred embodiment of the invention comprises reaction of a compound of formula IV,

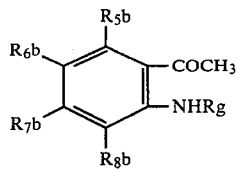

in which

R$_{5b}$, R$_{6b}$, R$_{7b}$ and R$_{8b}$ have the same significances as R$_5$, R$_6$, R$_7$ and R$_8$ above, save that an adjacent pair of R$_{5b}$, R$_{6b}$, R$_{7b}$ and R$_{8b}$ instead of forming a chain —COCH=C(COOH)—O—, form the pair of groups —COCH$_3$ and —OM, and Rg and M are as defined above, with a compound of formula I, and preferably with a dialkyl oxalate, e.g. a di- C 1 to 6 alkyl oxalate such as diethyl oxalate, and cyclising the resulting compound of formula III.

The compounds of formula IV, other than that in which Rg is hydrogen, R$_{6b}$ is acetyl and R$_{7b}$ is —OH, are new compounds and the invention also provides these compounds per se.

The compounds of formula IV may be made by Friedel Crafts acetylation of the appropriate aminophenol, which may if desired be in protected form, e.g. the amino group having been acylated (e.g. with a formyl, acetyl or pivaloyl group) and the hydroxy group having been alkylated, and subsequent removal of any remaining protecting groups. One compound of formula IV may if desired by converted to another, e.g. by O-alkenylation followed by Claisen rearrangement to produce the ring alkenylated derivative, which may then if desired be reduced to the corresponding ring alkyl compound.

The compounds of formula I are known compounds.

The quinolone-2-carboxylic acids produced by the process of the invention have a variety of uses, e.g. as chemical intermediates, and as pharmaceuticals. The compounds of formula II are particularly indicated for the treatment of allergic conditions. The compounds of Example 4(c) and Example 6, e.g. in their free acid or salt form, are new compounds and are particularly active or lacking in side effects compared to other compounds of similar structure.

In compounds of formula II we prefer each of Rg, R$_1$, R$_2$, R$_5$, R$_6$, R$_7$ and R$_8$, when they contain carbon, to contain up to 8, and preferably up to 4 carbon atoms. Specifically we prefer R$_5$, R$_6$, R$_7$ and R$_8$ to be selected from hydrogen, methoxy, propyl, allyl, methyl, ethyl, chlorine, bromine and hydroxy. We also prefer Rg to be hydrogen or alkyl C 1 to 4, e.g. ethyl. The —COCH=C(COOH)—O— chain may be bonded to the benzene ring in any sense and in any of the adjacent positions R$_5$, R$_6$, R$_7$, R$_8$. However, we prefer the chain to be bonded in the positions R$_6$ and R$_7$ the —O— part of the chain being in position R$_7$. We also prefer R$_8$ to be alkyl, e.g. propyl.

Pharmaceutically acceptable salts of the compounds of formula II include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the 2-(diethylamino)ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl)ether, e.g. the bis-2-oxapropan-1,3-diyl ester. The pharmaceutically acceptable acid addition salts of the basic esters, and also of those compounds in which one of R$_5$, R$_6$, R$_7$ and R$_8$ is a group —NR$_1$R$_2$, e.g. the hydrochloride, the hydrobromide, the oxalate, the maleate or the fumarate salts, may also be used. The amides may be, for example, unsubstituted or mono- or di- C 1 to 6 alkyl amides and may be made by conventional techniques, e.g. reaction of an ester of the corresponding acid with ammonia or an appropriate amine.

The invention is illustrated, but in no way limited by the following Examples in which the temperatures are in °C.

EXAMPLE 1

Ethyl 1,4-dihydro-4-oxo-quinoline-2-carboxylate 1.35 g (10 mMol) of 1-(2'-aminophenyl)ethanone was heated under reflux with 40 mMol of sodium ethoxide and 40 mMol of diethyl oxalate in 70 ml of ethanol for 2½ hr. The reaction mixture, which contained the sodium salt of ethyl (2-aminobenzoyl)pyruvic acid was poured into ice/hydrochloric acid and extracted with chloroform. Concentration to dryness and boiling with diethyl ether gave 1.25 g (58%) of the title product, mp 210°–212°.

EXAMPLE 2

Ethyl 1,4-dihydro-1-methyl-4-oxo-quinoline-2-carboxylate 149 mgs (1 mMol) of 1-(2'-methylaminophenyl)ethanone was heated under reflux with 4 mMol of sodium ethoxide and 4 mMol of diethyl oxalate in 7 ml of ethanol for 1½ hr. The reaction mixture, which contained the sodium salt of ethyl (2-N-methylaminobenzoyl)pyruvic acid was poured into dilute hydrochloric acid and extracted with chloroform. Evaporation to dryness and boiling the residue in diethyl ether afforded, after storing at 0°–5°, 160 mgs (70%) of the title product, mp 114°–5°.

EXAMPLE 3

Diethyl 6,9-dihydro-4,6-dioxo-4H-pyrano[3,2-g]quinoline-2,8-dicarboxylate

Diethyl 6,9-dihydro-4,6-dioxo-10-propyl-4H-pyrano[3,2g]-quinoline-2,8-dicarboxylate (a) 3-Acetamido-4,6-diacetylphenol (1) By a 'one-pot' procedure 3-Acetamidoanisole (2 moles) was added (in methylene chloride solution) to a stirred solution of aluminium chloride (2 moles) and acetyl chloride (2 moles) in dichloromethane at 0°–5° C. The mixture was then heated to reflux (for 69 hours) and added to ice/water after cooling to 25° C. After filtration the aqueous phase was extracted with methylene chloride, and the organic phase washed with water, dried, and concentrated.

Crystallisation of the residue from ethanol afforded the title compound in 34% yield, mp 201°–202° C.

(2) By sequential acetylations (i) 1-(4'-Acetamido-2'-hydroxy)ethanone

3-Acetamidoanisole (0.01 mole) in dry dichloromethane, was added to a solution of aluminium chloride (0.03 Mol) and acetyl chloride (0.03 Mol) in dry dichloromethane, at a temperature below 10° C. After stirring at 5° C. for 1 hour, the temperature was raised to, and held at, reflux until reaction was complete. The mixture was poured into water and the product isolated by filtration, yield 83%.

(ii) 3-Acetamido-4,6-diacetylphenol 1-(4'-Acetamido-2'-hydroxy)ethanone (500 g) was added to a cooled (10°–15° C.) solution of aluminium chloride (10 eq) and acetyl chloride (10 eq) in dichloromethane (7 l). The mixture was heated to, and maintained at, reflux for 40 hours. The mixture was cooled to 20° C. and added slowly to water. The solid was isolated by filtration and recrystallised from ethanol to afford the sub-title compound in 56% yield, mp 201°–202° C.

(b) 4,6-Diacetyl-3-aminophenol

3-Acetamido-4,6-diacetylphenol (250 g) was suspended in ethanol (2 l) containing conc. hydrochloric acid (200 ml) and heated on a steam bath for 5 hours. The mixture was allowed to cool, and the crystalline product isolated by filtration. Yield 91%, mp 227°–230° C.

(c) Diethyl 6,9-dihydro-4,6-dioxo-4H-pyrano[3,2-g]-quinoline-2,8-dicarboxylate

The product of step (b) (5 mmoles) and diethyl oxalate were heated at reflux in a solution of sodium ethoxide (50 mmoles) in ethanol (20 mls) for 3 hours.

The mixture, which contained the sodium salt of diethyl 4,4'-(2-amino-4-hydroxyphenylen-1,3-diyl)-bis(2,4-dioxobutanoate), was acidified with gaseous HCl, and refluxed for a further 1 hour. Pouring into water followed by extraction with dichloromethane gave, on concentration, a yellow solid in 79% yield.

Crystallisation from dimethylsulphoxide afforded the sub-title product mp 282°–284°.

(d) 3-Allyloxy-4,6-diacetyl aniline

Treatment of the product of step (b) (1.5 g) with $K_2CO_3$ (1 equivalent) and allyl bromide (2 equivalents) in dimethylformamide (20 ml) at 70° C. for 2½ hours followed by dilution with water at 70° C. afforded the sub-title product, as a pale yellow solid (83%) mp 131°–134°.

(e) 4,6-Diacetyl-3-amino-2-propylphenol

Heating of the product of step (d) (3.8 mmoles) in N-Methyl pyrrolidone (4 ml) under $N_2$ at 200° C. for 3 hours effected rearrangement to the 2-allyl compound. The reaction mixture was cooled to room temperature, diluted with ethanol (50 ml) and hydrogenated over Pd/C (5%) at atmospheric pressure. After removal of the catalyst by filtration, concentration afforded a residue containing N-methyl pyrrolidone. The mixture was diluted with water and the crude product isolated by filtration. Recrystallisation from ethanol gave the sub-title compound (82%) mp 138°–139°.

(f) Diethyl 6,9-dihydro-4,6-dioxo-10-propyl-4H-pyrano-[3,2-g]-quinoline-2,8-dicarboxylate Treatment of the product of step (e) (1 mmole) with sodium ethoxide (10 mmole), in ethanol (10 ml) containing diethyl oxalate (10 mmole) at reflux for 3 hours, followed by acidification of the mixture, which contained the sodium salt of diethyl 4,4'-(2-amino-4-hydroxy-3-propylphenylene-1,3-diyl)bis(2,4-dioxobutanoate), with gaseous HCl and heating under reflux for 1 hour afforded the subtitle compound which was isolated by dilution with water, extraction with chloroform, concentration and purification by column chromatography (yield 65%) mp 211°–212°.

(g) 6,9-Dihydro-4,6-dioxo-10-propyl-4H-pyrano[3,2-g]-quinoline-2,8-dicarboxylic acid The bis ester from step (f) (2.5 g) was refluxed with sodium bicarbonate (1.64 g) in ethanol (100 ml) and water (50 ml) for 1.5 hours. The whole was poured into water and acidified to precipitate a gelatinous solid. This was collected by filtration, refluxed with ethanol and the product was separated by centrifugation (1.4 g) mp 303°–304° C. dec. The structure of the product was confirmed by mass and NMR evidence.

(h) Disodium 6,9-dihydro-4,6-dioxo-10-propyl-4H-pyrano-[3,2-g]-quinoline-2,8-dicarboxylate The bis acid from step (g) (1.35 g) and sodium bicarbonate (0.661 g) in water (150 ml) were warmed and stirred until a clear solution was obtained. This solution was filtered and the filtrate was freeze dried to give 1.43 g of the required disodium salt.

Analysis: Found: C, 46.1%; H 4.0%; N 2.9%. $C_{17}H_{11}NO_7Na_2$ 12.5% $H_2O$ required: C 46.1%; H 3.8%; N 3.15%.

EXAMPLE 4

Diethyl 9-ethyl-6,9-dihydro-4,6-dioxo-10-propyl-4H-pyrano-[3,2-g]-quinoline-2,8-dicarboxylate (a) 4,6-Diacetyl-3-ethylaminophenol 3-Acetamido-4,6-diacetylphenol (0.01 mole) in N-methylpyrrolidone (NMP) (20 ml) was added to a cooled (<5° C.), stirred suspension of sodium hydride (0.022 mole) in NMP (5 ml). After 15 minutes the mixture was treated with ethyliodide (0.019 mole). After two hours at <5° C., the mixture was acidified with ethanol/conc. HCl (1:1, 20 ml) and heated to reflux for 2½ hours. The mixture was allowed to cool and the crystalline subtitle compound isolated by filtration. Yield 63%, mp 103°–104° C.

(b) 3-Allyloxy-4,6-diacetyl-N-ethylaniline

Allyl bromide (2 g) was added to a stirred solution of 4,6-diacetyl-3-ethylaminophenol (0.016 M) in dimethylformamide (30 ml) containing potassium carbonate (2 g). The mixture was heated at 60°–70° C. for two hours, and was then poured into water (100 ml), stirred, and the precipitated product isolated by filtration. Yield 93%, mp 82°–83° C.

(c) 4,6-Diacetyl-3-ethylamino-2-propylphenol

The product of step (b) (0.013 mole) was heated in NMP (25 ml) at reflux under nitrogen for 1 hour. After cooling to room temperature, the mixture was diluted with ethanol (25 ml), and hydrogenated over 5% Pd/C at 15–20 psi for 2½ hours. After filtration, the mixture was poured into water, the grey solid isolated by filtration, and recrystallised from ethanol to give the title compound. Yield 63%, mp 114°–115° C.

(d) Diethyl 9-ethyl-6,9-dihydro-4,6-dioxo-10-propyl-4H-pyrano[3,2-g]-quinoline-2,8-dicarboxylate A stirred mixture of 4,6-diacetyl-3-N-ethylamino-2-propylphenol (3.8 mmol), sodium ethoxide (30.4 mmol) and diethyl oxalate (26.5 mmol) in ethanol (50 ml/g of substrate) under nitrogen was heated under reflux for 3 hours. The reaction mixture, which contained the sodium salt of diethyl 4,4'-(2-ethylamino-4-hydroxy-3- propylphenylene-1,3-diyl)bis(2,4-dioxo-butanoate) was cooled, treated slowly with a 50:50 mixture of ethanol/concentrated hydrochloric acid, and heated under reflux for 0.5 hour.

The mixture was cooled, poured into ice and the precipitated solid filtered off and recrystallised from ethanol to give the title compound in 82% yield, mp 132°–134°.

EXAMPLE 5

Diethyl 9-ethyl-6,9-dihydro-4,6-dioxo-4H-pyrano[3,2-g]-quinoline-2,8-dicarboxylate A mixture of 4,6-diacetyl-3-N-ethylaminophenol (4.5 mmol) sodium ethoxide (36 mmol) and diethyl oxalate (36 mmol) in ethanol (50 ml/g of substrate) was heated under reflux and with stirring, in a nitrogen atmosphere, for 2 hours. The mixture, which contained the sodium salt of diethyl 4,4'-(2-ethylamino-4-hydroxyphenylene-1,3-diyl)bis(2,4-dioxo-butanoate) was then treated with a 50:50 mixture of ethanol/concentrated hydrochloric acid and heated under reflux for a further 20 minutes.

The reaction mixture wa poured into water, the yellow precipitate filtered off and purified by chromatography to afford the title compound in 44.8% yield, mp 193°–194°. The title compound may be converted to the free acid and the disodium salt thereof by conventional techniques.

EXAMPLE 6

The following compounds may also be made by the process of the invention.

Ethyl 1,4-dihydro-8-methyl-4-oxo-quinoline-2-carboxylate

Ethyl 6-n-butyl-1,4-dihydro-4-oxo-quinoline-2-carboxylate

Ethyl 1,4-dihydro-8-methoxy-4-oxo-quinoline-2-carboxylate

Ethyl 1,4-dihydro-8-methyl-4-oxo-3-propyl-quinolone-2-carboxylate

Ethyl 1,4-dihydro-6-methyl-4-oxo-quinoline-2-carboxylate

Ethyl 4-ethyl-1,4-dihydro-4-oxo-quinoline-2-carboxylate

Ethyl 6-chloro-1,4-dihydro-4-oxo-quinoline-2-carboxylate

Ethyl 8-chloro-1,4-dihydro-4-oxo-quinoline-2-carboxylate

We claim:

1. A compound having the formula

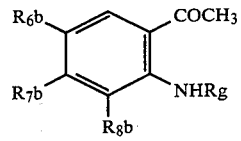

in which
$R_{6b}$ and $R_{7b}$ together form a chain —COCH=C—(COOH)—O—, or a pharmaceutically acceptable salt or a lower alkyl ester thereof, or form the pair of groups —COCH$_3$ and —OM, respectively, $R_g$ and $R_{8b}$, which may be the same or different, each represent hydrogen, alkyl or alkenyl, the alkyl and alkenyl groups each containing up to eight carbon atoms, and M is hydrogen or an alkali metal, provided that when $R_g$ is hydrogen, $R_{6b}$ is acetyl and $R_{8b}$ is hydrogen, then $R_{7b}$ is other than —OH.

2. A compound according to claim 1, wherein $R_{6b}$ and $R_{7b}$ form the pair of groups —COCH$_3$ and —OM.

3. A compound according to claim 2 which is 4,6-diacetyl-3-amino-2-propylphenol, or 4,6-diacetyl-3-ethylamino-2-propylphenol.

* * * * *